United States Patent [19]

Claremon

[11] Patent Number: 4,908,452

[45] Date of Patent: Mar. 13, 1990

[54] PROCESS FOR PREPARING NITRILES

[75] Inventor: David A. Claremon, Audubon, Pa.

[73] Assignee: Merck & Co., Inc., Rahway, N.J.

[21] Appl. No.: 135,866

[22] Filed: Dec. 21, 1987

[51] Int. Cl.$^4$ .................. C07D 303/46; C07D 213/82; C07C 120/10
[52] U.S. Cl. ..................................... 546/286; 544/204; 546/228; 548/341; 549/474; 549/548; 558/312; 558/313
[58] Field of Search .................. 560/13, 148; 549/548; 558/312, 313; 546/286

[56] References Cited

U.S. PATENT DOCUMENTS

| | | | |
|---|---|---|---|
| 2,295,406 | 9/1942 | Jolly | 558/314 |
| 3,385,866 | 5/1968 | Lohaus et al. | 558/313 X |
| 3,646,103 | 2/1972 | Luecke | 558/312 |
| 3,850,974 | 11/1974 | Lichtenwalter et al. | 558/313 X |
| 4,605,521 | 8/1986 | Eubanks et al. | 558/313 |
| 4,654,426 | 3/1987 | Bisacchi et al. | 549/548 |

OTHER PUBLICATIONS

Claremon & Phillips; Tetrahedron Letters, 24(1988), pp. 2155–2158.
Mai et al; Tetrahedron Letters, 27 (1986), pp. 2203–2206.
Thompson et al.; J. of Med. Chem. 29 (1986), pp. 104–111.
Burgess et al.; J. Org. Chem., 38 (1973), pp. 26–31.
Burgess et al.; Org. Syn., 56 (1977), pp. 40–43.
Fieser et al.; Reagents for Organic Synthesis, vol. 4 (1974), pp. 227, 228, 343, 344 and vol. 5 (1975), pp. 442, 443.

Primary Examiner—Joseph P. Brust
Attorney, Agent, or Firm—Alice O. Robertson; Joseph F. DiPrima

[57] ABSTRACT

A facile and mild process for the preparation of nitriles from reagent sensitive primary carboxamides is described. The process utilizes a (carboxysulfamoyl)ammonium hydroxide compound as the dehydrating agent. It is useful for preparing nitriles which have present other groups which are sensitive to the more conventional methods of dehydration or to other methods of nitrile synthesis. Some novel nitriles prepared by the new method are also described.

12 Claims, No Drawings

PROCESS FOR PREPARING NITRILES

BACKGROUND OF THE INVENTION

Nitriles have long been important not only as intermediates in organic synthesis, but many times of themselves. Recently, it was reported by S. A. Thompson, et al., in J. Am. Chem. Soc. 29, 104 (1985) that nitriles, especially analogs of enzyme substrates having a carboxamide group in its structure, can act as protease enzyme inhibitors. Protease enzymes play critically important roles in initiating, continuing or terminating a wide variety biological processes such as blood coagulation, complement activation, viral replication and in disease processes such as inflammatory and tissue degenerative diseases, tumor metastasis and the like. Other enzymes playing important roles in biological processes act on substrates having substituted amide groups in their structure. It is not unlikely that many enzymes acting on substrates having a substituted amide group may be inhibited or have the activity altered or modified by a substrate in which the amide group in the vicinity of a scissile bond is replaced with nitrile, i.e., by nitrile analogs of specific substrates.

The work of Thompson et al suggests that there may be infinite possibilities for nitriles corresponding to naturally occurring complex amides, acids, esters and other acid derivatives that should be investigated in connection with the search for new therapeutic agents which can be used to prevent, modify or reverse undesirable biological processes in the prevention and cure of diseases. Moreover, a number of compounds having a nitrile group together with another functional group are biologically active. A facile method for preparing nitriles is desired so that new inhibitors which may be one or more of the future drugs may not be overlooked because of difficulty of synthesis. Thus, a method of synthesis for nitriles, particularly a ready method for converting carboxamides to the corresponding nitriles would be highly desirable.

One convenient approach to the synthesis of nitriles is the dehydration of carboxamides. However, reagents which are generally employed to accomplish this dehydration are generally inappropriate in the synthesis of complex polyfunctional compounds which require mild conditions in their synthesis. the functional groups may be protected, protection of intermediates entails the extra steps of putting on a protecting group and of afterwards removing the protecting group. Not only are extra steps necessitated but at times the protection/deprotection procedure can adversely affect the desired structure. Recently, the use of liquid "diphosgene", trichloromethyl chloroformate, for transforming certain carboxamides to nitriles has been reported. (K. Mai et al, in Tetrahedron Letters, 1986 2203.) While the reagent is reported to be useful with a wide variety carboxamides, it has been found not to be usable with certain compounds such as those having an alcoholic hydroxyl group or even with simple heteroaromatic compounds such as nicotinamide. Moreover, the byproduct of the reaction is a highly undesirable toxic gas, namely, phosgene. This would be especially undesirable where production of significant quantities of nitrile is desired. Further, the reagent is not seen to be useful for structures containing alcoholic hydroxyls or epoxide rings, the latter being especially sensitive to acidic reagents.

Methyl (carboxysulfamoyl)triethylammonium hydroxide inner salt

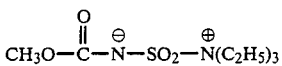

often referred to as Burgess reagent, was used by Burgess and coworkers to convert tertiary and secondary alcohols to olefins and primary alcohols to urethanes. However other uses of this reagent are not known.

STATEMENT OF THE INVENTION

According to the present invention there has been discovered a simple, single step process for preparing a nitrile compound in good yields and high purity by treating the corresponding carboxamide compound with a (carboxysulfamoyl)ammonium hydroxide compound. By a "single step" process is meant that between the placement of the reactants in the reaction vessel and recovery of the product therefrom, no manipulative procedures for isolation of intermediate is necessary.

DETAILED DESCRIPTION OF THE INVENTION

In the present invention, a nitrile compound represented by the formula

may be obtained in good yield by contacting a carboxamide compound represented by the formula

with a (carboxysulfamoyl)ammonium hydroxide compound represented by the formula

in an anhydrous, inert atmosphere for time sufficient to effect dehydration.

In the foregoing and succeeding formulas, R, R' and X are as hereinafter defined. R may be an aliphatic, aromatic or a heterocyclic radical provided that R does not bear a primary or secondary amino or a sulfhydryl or primary hydroxyl group. The attaching carbon of R may be (a) a primary, secondary or tertiary carbon linked to other carbon atoms in a saturated or unsaturated straight chain or cyclic linkage, (b) part of an epoxide or other non aromatic heterocyclic ring, or (c) part of an aromatic or heteroaromatic ring. When R is a saturated or unsaturated straight chain radical, it may have up to about 20 carbons or more, and it may be interspersed with hetero atoms and with double or triple bonded unsaturation; when it is a cyclic aliphatic radical it may be heterocyclic or carbocyclic of ring size of from about 3 to 7 atoms or may be larger such as in some natural product rings; when it is aromatic carbocyclic or heterocyclic it will generally have a single ring size of about 5 or 6 atoms but may be part of a condensed ring or other polycyclic ring. R may have substituents which provide functional groups such as ketones, substituted amides, alcohols, carboxylic or sulfonic acid esters, phenols, ethers and the like on an alkyl, or alkylene chain or on an aromatic ring; further it may have one or more of other substituents such as halo, cyano, haloalkyl, phenyl, naphthyl, benzyl, phenylethyl and nitro provided that there is no unsubstituted amino group or sulfhydryl group and preferably no primary hydroxyl group.

Each R' is independently lower alkyl, or aralkyl. By "lower alkyl" is meant from 1 to 4 carbon atoms. By "aralkyl" is meant aryl substituted lower-alkyl, preferably phenyl-substituted lower alkyl or substituted phenyl-substituted lower alkyl. The most preferred aralkyl groups are benzyl and phenylethyl.

Since in the absence of a primary or secondary amino, a primary hydroxyl, or a sulfhydryl group, the reaction may be carried out without the need for a protecting group, for complex compounds lacking these groups, an extremely facile method which avoids the necessity for protecting and deprotecting is provided. In addition, the present process is free of toxic by products such as phosgene and further, the by-products are water-soluble materials which may be washed readily from the reaction mixture.

Representative of the diverse structures which R may be are the following radicals

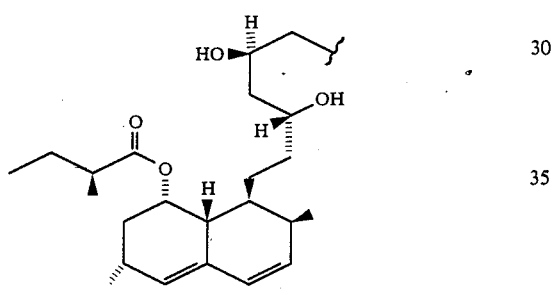

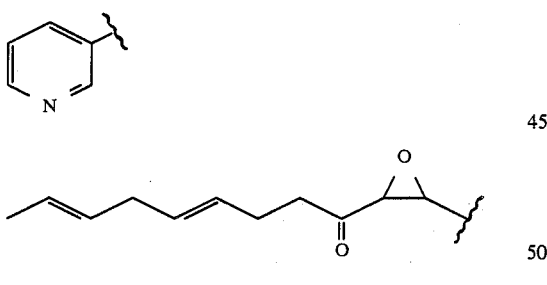

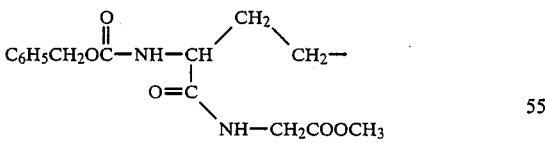

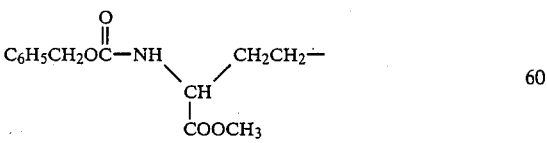

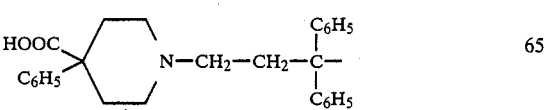

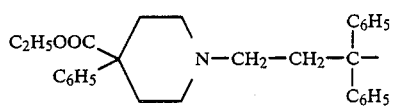

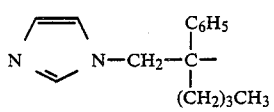

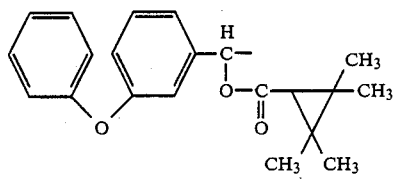

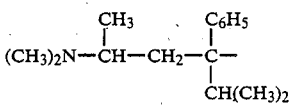

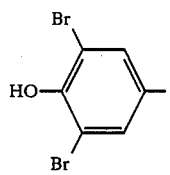

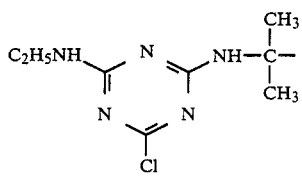

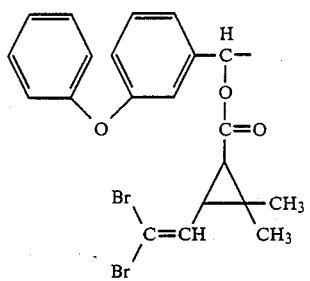

Other simpler structures such as the following are embraced within R, although for some of the simpler structures other methods may be available

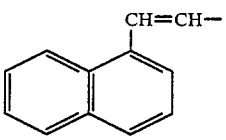

C₆H₅CH=CH—

4-HO—C₆H₄—

(CH₃)₃C—

-continued

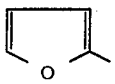

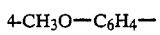

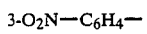

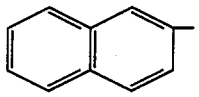

Compounds obtained by this process include nitrile analogs of known inhibitors or nitrile analogs of substrates of various enzymes some of which have been found to have superior activity. Thus, the process is also useful as a biochemical and pharmacological tool for investigating new enzyme inhibitors, particularly those in which the enzyme substrate are known to have carboxamide group. It is further useful for obtaining totally new enzyme inhibitors where such is not yet known or new alternative inhibitors which may provide better therapeutic promise.

In the process of the present invention, the dehydrating agent is a (carboxysulfamoyl)ammonium hydroxide compound (Formula III). When this reagent is employed under the conditions contemplated according to the present invention, the reaction proceeds smoothly with the formation of the nitrile from the corresponding carboxamide. Moreover, contrary to what might be expected from the teachings in the literature, under the conditions of the present invention there is no dehydration of an alcoholic group to an olefin linkage. This makes possible the synthesis of enzyme inhibitors and substrate analogs which include hydroxyl groups in their complex structure. However, it has been found that the process is not applicable to compounds having primary or secondary amino groups or a sulfhydryl group, and preferably also not to compounds having primary hydroxyl.

The (carboxysulfamoyl)ammonium hydroxide compound is employed in molar excess. From about 2 to 5 molar excess is satisfactory. The preferred (carboxysulfamoyl)ammonium hydroxide compound is methyl (carboxysulfamoyl)triethylammonium hydroxide.

The reaction is carried out in an inert solvent. It is insensitive to solvent variation and a large number of solvents are suitable. Suitable solvents include methylene chloride, ethylene dichloride, chloroform, carbon tetrachloride, tetrahydrofuran, dioxane, dimethylformamide, benzene and the like. The solvent should be anhydrous since the reaction is sensitive to moisture. Preferably, the solvent is distilled from a drying agent such as calcium hydride immediately prior to use.

The reaction is carried out in an inert atmosphere such as in an atmosphere of argon or nitrogen.

A suitable temperature for carrying out the reaction is in the range of from about −10° to 80° C. Ambient temperature is conveniently employed and is an advantage of the present process.

The reaction may be carried out over a period of several hours.

A preferred embodiment of the present invention comprises adding methyl (carboxysulfamoyl)-triethylammonium hydroxide portionwise to a stirred suspension or solution of a carboxamide compound, $RCONH_2$ at ambient temperature under an inert atmosphere and continuing the stirring for time sufficient to complete the reaction with the formation of the desired nitrile compound, RCN. If the starting carboxamide is suspended in the reaction mixture, there generally will be a disappearance of the solid when the conversion is complete. Completion of the reaction is most conveniently determined by thin layer chromatography (TLC) of a reaction mixture sample.

After completion of the reaction, the product nitrile may be recovered and purified by conventional procedures. Generally, the reaction mixture is applied to a silica gel column and purified by chromatography. Some of the reaction mixture solvent may be vaporized before carrying out this step. Solvent mixtures suitable for elution include ethyl acetate/hexane, ether/hexane, acetone/methylene chloride, methanol/methylene chloride. 50 percent ethyl acetate/hexane is preferred. After chromatography, the product is recovered from the eluate by conventional procedures.

The following examples illustrate the invention but are not to be construed as limiting.

EXAMPLE I

Preparation of [1S-[1α(R*), 3α, 7β, 8β(3S*,5S*),8αβ]]-2-Methylbutanoic acid 8-(6-cyano-3,5-dihydroxyhexyl)-1,2,3,7,8,8a-hexahydro-3,7-dimethyl-1-naphthalenyl ester (lovastatin nitrile)

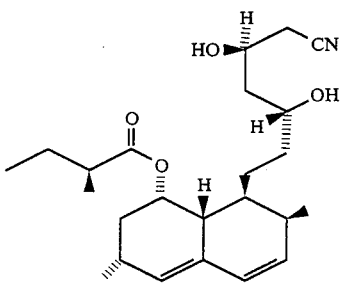

To a Stirred solution of 125 milligrams (0.30 millimole) of lovastatin (mevinolin) amide, in 1.5 milliliters of anhydrous methylene chloride (freshly distilled from calcium hydride) in an atmosphere of argon was added at 25° C., methyl (carboxysulfamoyl)triethylammonium hydroxide inner salt (Burgess reagent) in five 50 milligram portions (1.05 millimoles) over a period of 2 hours. After completion of the addition, stirring was continued an additional 15 minutes to complete the dehydration to a nitrile product, and the mixture containing the nitrile product then applied to a silica gel column. Flash chromatography with 50 percent ethyl acetate in hexane was employed to purify the product and to obtain 99 milligrams (82 percent yield) of [1S-[1α(R*),3α, 7β, 8β(3S*,5S*),8αβ]]-2-methylbutanoic acid 8-(6 carboxamide-3,5-dihydroxyhexyl)-1,2,3,7,8,-8a-hexahydro-3,7-dimethyl-1-naphthalenyl ester as a white crystalline solid having the following physical properties:

Anal Calcd for $C_{24}H_{37}NO_4$: C, 71.43; H, 9.24; N 3.47, Found: C, 71.31; H 9.10; N 3.30.

Rf=0.22 (silica, 50% ethyl acetate in hexane) $^1$H NMR (300 MHz., CDCl$_3$) δ=0.89 (d, J=7.0 Hz, 3H) 0.90 (t, J=8.0 Hz, 3H) 1.11(d, J=8.0 Hz, 3H) 1.13 (d, J=7.1 Hz, 3H) 1.20–2.05 (m, 11H) 2.20–2.56 (m, 4H), 2.53 (d, J=6.4 Hz, 2H), 2.83 (d, J=4.3 Hz, 1H, exchangeable), 3.82 (m, 1H), 4.14 (m, 1H), 4.31 (d, J=1.4 Hz, 1H, exchangeable) 5.51 (m, 2H), 5.78 (dd, J=6.3, 10.0 Hz, 1H) 6.00 (d, J=10.0 Hz, 1H) ppm. IR (CHCl$_3$)$_{2\gamma}$=3490(m, OH, 2270 (w, nitrile), 1725 (s, ester carbonyl) cm$^{-1}$.

The lovastatin amide starting material was that which had been prepared by intimately contacting 2 methylbutanoic acid 1,2,3,7,8,8a-hexahydro-3,7-dimethyl-8-[2-(tetrahydro-4-hydroxy-6-oxo-2H-pyran-2-yl)ethyl]-1-naphthalenyl ester (mevinolin or lovastatin) with excess anhydrous ammonia in ethanol at 50° C. for 2 hours and at 25° C. overnight, thereafter concentrating the reaction product mixture to obtain a crude lovastatin amide product which was recrystallized from toluene to obtain purified amide.

EXAMPLE II

Preparation of 3-(1-oxo-4,7-nonadienyl)oxirane-carbonitrile (ceruleninonitrile)

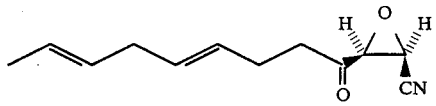

In an operation carried out in a manner similar to that described in Example I, six 24 milligram portions of methyl (carboxysulfamoyl)-triethylammonium hydroxide was added over a 2-hour period to a solution of 45 milligrams (0.20 millimole) of cerulenin 3-(1-oxo-4,7-nonadienyl)oxiranecarboxamide; obtained from Sigma) in 1 milliliter of dry, freshly distilled methylene chloride. At the time of completion of the final addition, thin layer chromatography (TLC) showed that all of the cerulenin had reacted.

The reaction mixture was applied directly to a silica gel column and subjected to flash chromatography eluting with 50 percent ethyl acetate/hexane to obtain in the eluate 36 milligrams (88 percent yield) of 3-(1-oxo-4,7-nonadienyl)-oxiranecarbonitrile as an oil. The product crystallized in the freezer but melted below 35° C.

EXAMPLE III

Preparation of S-4-Cyano-2-[[(phenylmethoxy)carbonyl]-amino]-butanoic acid methyl ester

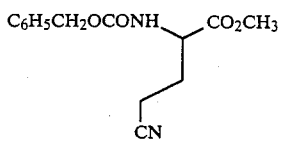

In a similar operation, seven 48 milligram (0.20 mmol) portions of methyl (carboxysulfamoyl)triethylammonium hydroxide was added over 2 hours and 40 minutes to a suspension of 0.147 gram (0.50 millimole) of methyl S-4-cyano-2-[[(phenylmethoxy)carbonyl]-amino]butanote compound (carboxamide compound). By the time the addition was complete, all of the car-boxamide compound had dissolved and TLC showed that the compound had reacted.

The reaction mixture was applied directly to a silica gel column and eluted with 50 percent ethyl acetate/hexane in a flash chromatographic operation and the eluate concentrated to obtain 0.137 gram (99 percent) of oil which was further concentrated to obtain a solid which was recrystallized from ether/hexane to obtain 0.121 gram of a S-4-cyano-2-[[(phenylmethoxy)carbonyl]aminobutanoic acid methyl ester product of m.p. 49°–50° C.

Anal. Calcd for C$_{14}$H$_{16}$N$_2$O$_4$: N, 10.04; C, 60.86; H, 5.84; Found: N, 10.16; C, 61.04; H, 5.80.

$[α]_D$ $_{obs}$= −18.40, $[α]_D23_{lit.}$= −18.4° (c=0.60 g/100 cc, MeOH).

EXAMPLE IV

Preparation of S-4cyano-2-[[(phenylmethoxy)carbonyl-]amino]-butyl]glycine methyl ester

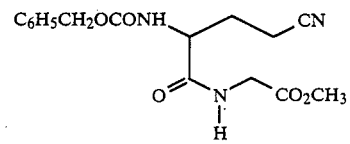

In an operation carried out in a manner similar to the foregoing examples, five 48 milligram (0.20 mmole) portions of methyl (carboxysulfamoyl)-triethylammonium hydroxide was added over a one hour, 40 minute period to a suspension of S-4-carboxamide-2-[[(phenyl-methoxy)carbonyl)amino]butyl]glycine methyl ester (carboxamide compound) in tetrahydrofuran. By the time of completion of the addition, all of the carboxamide compound had gone into solution and TLC analysis indicated that all of the compound had reacted. The reaction mixture was then concentrated and the residue dissolved in methylene chloride and applied to a silica gel column and flash chromatographed employing 50 percent ethyl acetate/hexane as eluting agent to obtain 0.148 gram (89 percent yield) of the S-4-cyano-2-[[(phenylmethoxy)carbonyl]amino]butyl]glycine methyl ester product as a white solid. The product after recrystallization had a melting point of 118°–119.5° C. The elemental analysis were as follows.

Calcd for C$_{16}$H$_{19}$N$_3$O$_5$: N, 12.61; C, 57.65; H, 5.75. Found: N, 12.61; C, 57.61; H, 5.71.

The starting benzyloxycarbonyl-glutaminylglycine methyl ester was prepared employing the solid phase peptide synthesis of Merrifield. (G. Barany & R. B. Merrifield, "The Peptides," Vol 2, p. 1, New York, Academic Press, 1979; M. Bodanszky, "Principles of Peptide Synthesis," chapter VII, Springer-Verlag, Berlin, 1984). In carrying out the synthesis, N-t-BOC-glycine-PAM resin ester (N-tert-butoxycarbonylglycine phenylacetamidomethyl resin ester from Sigma Chemical Co., St. Louis, Mo.) was first treated with trifluoroacetic acid to remove the butoxycarbonyl protecting group, the resulting glycine PAM resin washed with dimethylformamidimethylene chloride, neutralized with triethylamine and thereafter coupled with N-benzyloxycarbonylglutamine with the aid of dicyclohexylcarbodiimide and hydroxybenztriazole. Thereafter, the resulting peptide was removed from the resin with 20 percent triethylamine in methanol to obtain benzyloxycarbonylglutaminylglycine methyl ester.

EXAMPLE V

Preparation of 3-Cyanopyridine

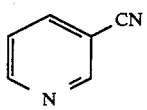

In a similar manner, 61 milligrams (0.5 millimole) of nicotinamide was intimately contacted with 200 milligrams (1.7 millimoles) of methyl (carboxysulfamoyl)-triethylammonium hydroxide in 1 milliliter of tetrahydrofuran at room temperature over 2.5 hours to obtain a 3-cyanopyridine product in the reaction mixture.

The mixture was then diluted with ethyl acetate and washed successively with aqueous potassium carbonate, water and brine and then dried over sodium sulfate. The dried solution (after filtering the drying agent) was concentrated to obtain the 3-cyanopyridine product as a solid residue. The product was identical to authentic 3-cyanopyridine by melting point, NMR spectroscopy and thin layer chromatography.

The process of the present invention is especially useful for the preparation of

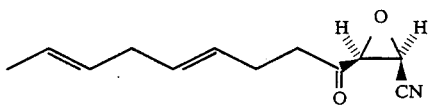

The compound is a nitrile analog of Cerulenin, a well known antibiotic, and which may be named 3-(1-oxo-4,7-nonadienyl)oxiranecarbonitrile. The compound has also been found to have inhibitory activity against Factor XIIIa, a plasma transglutaminase enzyme which catalyzes a number of reactions stabilizing blood clots and when the compound is employed with a plasminogen activator is useful in thrombolytic therapy.

The Factor XIIIa inhibitor activity may be determined by an assay described in Methods in Enzymology, Vol. 45, Ch 15, pages 177-191 (1976) and using Factor XIII isolated from human plasma. Briefly, the assay is carried out by adding a substrate mixture of $^{14}$C-putrescine and N,N-dimethyl-casein to an Factor XIII assay mixture previously prepared by adding thrombin and dithiothreitol to Factor XIII in glycerol/water and tris(hydroxymethyl)aminomethane hydrochloride and then adding calcium ions, thereafter, incubating at 37° for 20 minutes, withdrawing samples to a filter disk, precipitating the casein with trichloracetic acid and then counting to determine the extent of incorporation of inhibitor of $^{14}$C-putrescine in casein. The result for 3-(1-oxo-4,7-nonadienyl)-oxiranecarbonitrile was 60 percent inhibition at 3 mM.

What is claimed is:

1. A process for preparing by selective dehydration, a nitrile compound from the corresponding carboxamide compound, said nitrile compound represented by the formula

R—C≡N  (I)

which comprises intimately mixing and causing to react a carboxamide compound represented by the formula

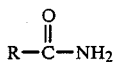 (II)

with a molar excess of a (carboxysulfamoyl)ammonium hydroxide compound represented by the formula

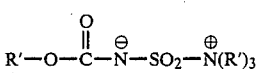 (III)

at temperatures in the range of from −10° C. to 80° C. under anhydrous conditions in an inert solvent and in an inert atmosphere for time sufficient to effect dehydration to form the corresponding nitrile, wherein in the foregoing formulas, R is selected from the group consisting of

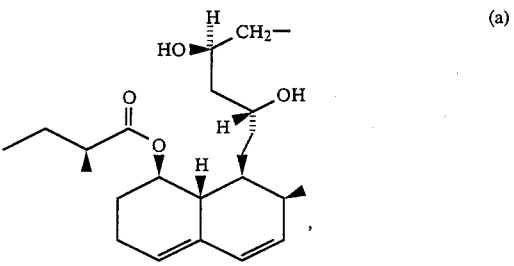 (a)

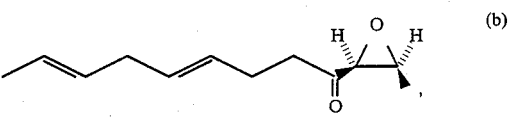 (b)

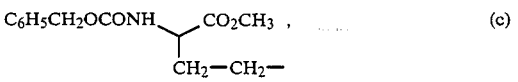 (c)

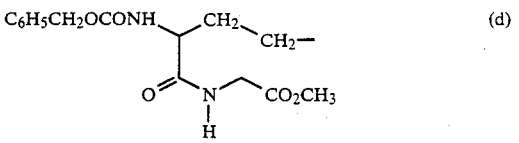 (d)

and

 (e)

and each R' is independently lower alkyl from 1 to 4 carbon atoms, benzyl or phenylethyl.

2. A process according to claim 1 wherein the (carboxysulfamoyl)ammonium compound is methyl (carboxysulfamoyl)triethylammonium hydroxide.

3. A process according to claim 2 wherein from 2 to 5 molar excess of methyl (carboxysulfamoyl)-triethylammonium hydroxide is employed.

4. A process according to claim I wherein the reaction is carried out at ambient temperature.

5. A process according to claim 1 in which R is

11

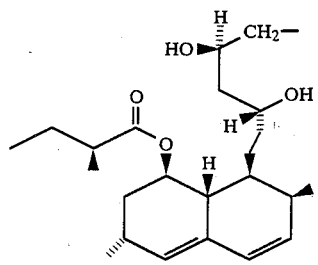

and R' is methyl.

6. A process according to claim 1 in which R is

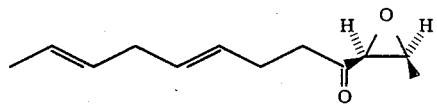

and R' is methyl.

7. A process according to claim 1 in which R is

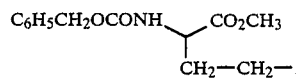

and R' is methyl.

8. A process according to claim 1 in which R is

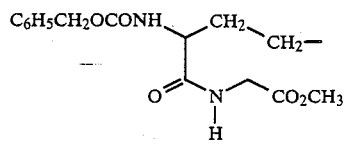

and R' is methyl.

9. A process according to claim 1 in which R is

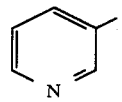

and R' is methyl.

10. A process for preparing

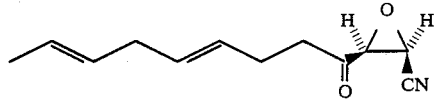

comprising intimately contacting

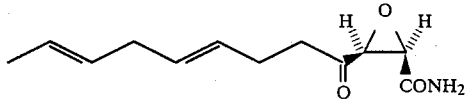

with a molar excess of methyl (carboxysulfamoyl)triethylammonium hydroxide at ambient temperature in an inert solvent and inert atmosphere for time sufficient to effect dehydration.

11. The compound 3-(1-oxo-4,7-nonadienyl)-oxiranecarbonitrile.

12. A compound according to claim 11 which is an isomer represented by the formula

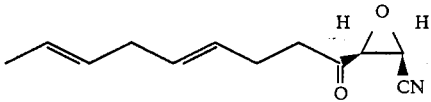

* * * * *